(12) United States Patent
Rasmussen

(10) Patent No.: US 6,761,693 B1
(45) Date of Patent: Jul. 13, 2004

(54) DEVICE AND METHOD FOR DETECTING OPENING OF PASSAGE IN BODILY CAVITY

(75) Inventor: Steen B. Rasmussen, Lynge (DK)

(73) Assignee: Rhinometrics A/S, Lynge (DK)

( * ) Notice: Subject to any disclaimer, the term of this patent is extended or adjusted under 35 U.S.C. 154(b) by 36 days.

(21) Appl. No.: 10/111,759

(22) PCT Filed: Oct. 31, 2000

(86) PCT No.: PCT/DK00/00603

§ 371 (c)(1),
(2), (4) Date: Jun. 3, 2002

(87) PCT Pub. No.: WO01/32082

PCT Pub. Date: May 10, 2001

(30) Foreign Application Priority Data

Nov. 2, 1999 (DK) .......................................... 1999 01586

(51) Int. Cl.$^7$ ............................... A61B 8/00; A61B 5/08
(52) U.S. Cl. ..................................... 600/462; 600/529
(58) Field of Search ................................ 600/529, 300, 600/462, 532, 533, 452, 568; 129/898, 207.14, 207.15

(56) References Cited

U.S. PATENT DOCUMENTS

| | | | | |
|---|---|---|---|---|
| 4,326,416 A | * | 4/1982 | Fredberg | 600/533 |
| 5,316,002 A | * | 5/1994 | Jackson et al. | 600/463 |
| 5,331,967 A | * | 7/1994 | Akerson | 600/529 |
| 5,823,965 A | * | 10/1998 | Rasmussen | 600/462 |
| 5,882,314 A | * | 3/1999 | Fredberg et al. | 600/529 |
| 6,443,907 B1 | * | 9/2002 | Mansy et al. | 600/529 |

* cited by examiner

Primary Examiner—Mary Beth Jones
Assistant Examiner—Navin Natnithithadha
(74) Attorney, Agent, or Firm—Dykema Gossett PLLC

(57) ABSTRACT

A method and device for detecting opening of a passage in a bodily cavity, the device including an electric signal source; a first transducer for converting an electric signal from the electric signal source into an acoustic signal; a second transducer for reception of the acoustic signal; and where the first and the second transducer are placed on respective opposite sides of the obstruction in the cavity. In the method an acoustic signal is supplied at one side of the obstruction and received at the other side of the obstruction, when the passage is open.

4 Claims, 2 Drawing Sheets

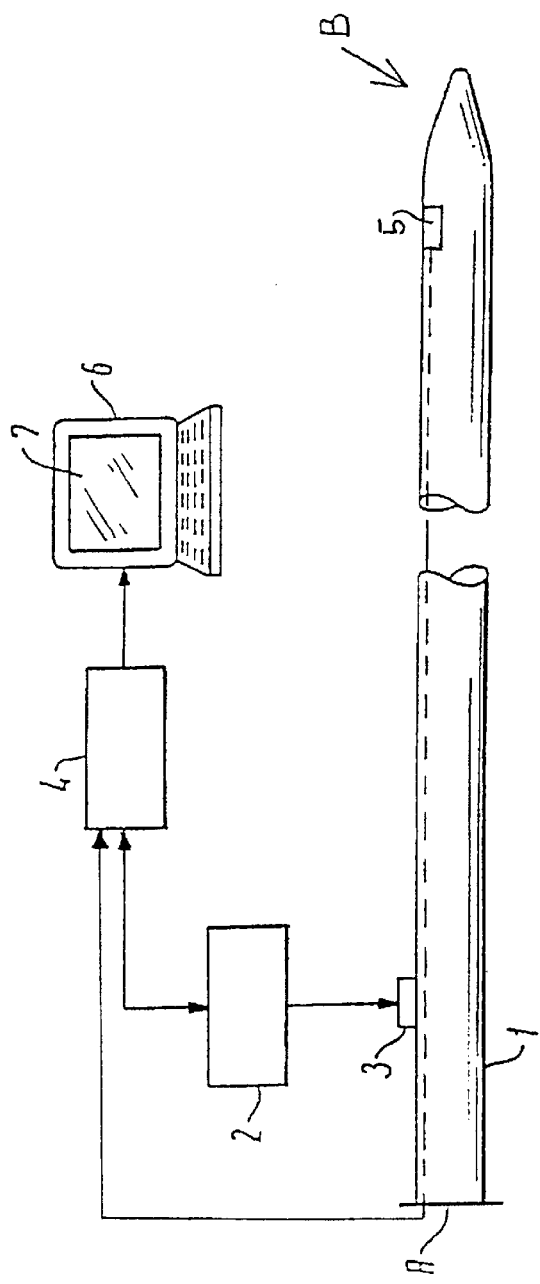
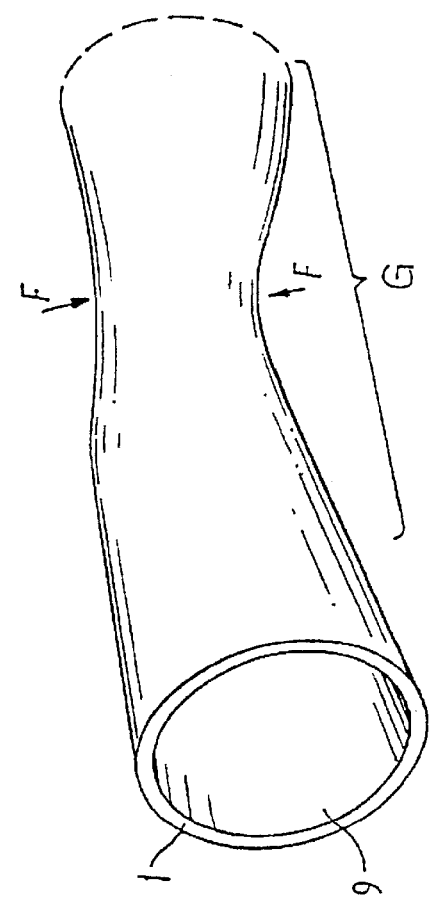
FIG.1
FIG.2

DEVICE AND METHOD FOR DETECTING OPENING OF PASSAGE IN BODILY CAVITY

FIELD OF THE INVENTION

The invention relates to the field of medicine where bodily cavities are examined and where restrictions or obstructions are diagnosed or identified. Such restrictions may when present form open or closed passages dependent on the pressure on either side of the passage and dependent on the activity of the patient in question. One example of such bodily cavity is the respiratory passage. The tongue and the soft palate may often form an obstruction when these relax during sleep. The condition is called obstructive sleep apnea (OSA) and is characterized by the patient not breathing for a longer or shorter period of time. Obviously this inflicts a significant risk for the patient's health and in severe cases for the patient's life. Other bodily cavities may contain an obstruction and hence require examination of these.

Although the invention is in the following only explained in connection with its use in the respiratory passage, it should be appreciated that the invention finds use in connection with other bodily cavities as well.

BACKGROUND OF THE INVENTION

In order to remedy some of the risk of the sleep apnea an apparatus has been developed which applies air under pressure to all the patient's respiratory system during sleep. These apparatuses are often designated CPAP machines after the therapy, which is called Continuous Positive Airflow Pressure therapy. Other products designations are used for apparatuses having a similar function. VPAP and DIPAP are examples of such. This pressure helps maintain open or helps opening any restrictions in the patient's respiratory passages and does in this manner help the patient in breathing. The patient may by use of such device reduce the risk of suffocating and can at the same time obtain the necessary rest or sleep. The pressurized air is supplied through a mask, which the patient wears over the mouth and/or nose. Many patients may be helped by means of this therapy and the related apparatuses as an alternative to surgical treatment. In order to fit the apparatus correctly to the individual patient, the pressure necessary for performing the opening of one or more of the restrictions in passage must be identified and the apparatus must be adjusted to supply the necessary pressure within a given upper and lower limit. The fitting of the apparatus with the correct pressure, which is individual for each patient, is very important as an incorrect too high pressure may lead to nasal dryness, discomfort and swallowing of air. It is obvious that it is desirous to keep the airflow as low as possible. On the other hand, a to low pressure will not provide the necessary help to the patient. Moreover, it is well known that the required pressure for each patient may change over time as the physiological demands changes. This does require frequently follow up on the adjustment in order to have the optimal level of pressure delivered. Hitherto this pressure adjustment has been carried out during a sleep study and has been carried out by a trained person who adjusts the pressure until it is as high as required for abolishing apnea, hypoapnea and snoring. In other words, the pressure is adjusted according to some symptoms of the closed passage and not necessarily according to the actual desired condition, namely the opening of the passage. It is obvious that the previously used method may lead to an adjustment of the pressure which is either too low or too high, where the later is more often the case, with the consequences described above.

Another method used comprises observation of the counter pressure in the system. When the counter pressure decreases, this is taken as an indication of opening of the passage. This method has a degree of uncertainty in respect of correct detection of the opening in the bodily cavity.

Obviously, since this previously known apparatus and the related fitting methods for the apparatus leaves some drawbacks due to a significant uncertainty about the pressure determination and as the previously known method is rather time consuming, there is a need for improving the previously known method and apparatus.

A further situation where an obstruction may be diagnosed is in the examining equipment as disclosed in U.S. Pat. No. 5,823,965. This previously known apparatus is adapted for examination of the cross section of a bodily cavity.

It is therefore one objective of the invention to provide an apparatus which facilitates the determination of the opening of a passage in a bodily cavity by making a more accurate determination possible in a less time consuming process. It is a further objective of the invention to provide a method which facilitates the determination of the opening of a closed passage in a bodily cavity by making a more accurate determination possible in a less time consuming process.

SUMMARY OF THE INVENTION

According to the invention the first objective is achieved by an, apparatus which comprises an electric signal source; a first transducer for converting an electric signal from the electric signal source into an acoustic signal; a second transducer for reception of the acoustic signal; and where the first and the second transducer are adapted to be placed on respective sides of the obstruction.

By means of the apparatus according to the invention, the opening can be determined very accurately as the reception signal is sampled and as the opening of the passage gives rise to a significant and unambiguous change in the received signal. The apparatus according to the invention may also be used in connection with the method and apparatus disclosed in U.S. Pat. No. 5,823,965 order hereby to detect an obstruction in the bodily cavity. It is obvious that an erroneous diagnosis can be avoided by this combination.

In a preferred embodiment the device comprises a hose to be introduced into the bodily cavity beyond the obstruction and where the hose has at least in a zone for placing at the passage an outer wall of a soft or elastomeric material. Hereby the electrical signal means are controllable in a reliable manner and the soft or flexible hose has little or no impact on the measuring accuracy.

In a further preferred embodiment the hose is closed at the distal end. This facilitates the introduction of the hose by means of as guide wire.

In a still further preferred embodiment the apparatus comprises means for supplying a pressurized medium into the cavity. Hereby a necessary opening pressure can be supplied simultaneously with the measuring and the necessary opening pressure may be determined.

In a preferred embodiment the hose has a separate cavity for supplying the pressurized medium beyond a restriction in the bodily cavity.

In a preferred embodiment the first, the second or both transducers are integrated in the hose. This provides for a safe handling of the apparatus and minimizes the risk of breaking the equipment and making erroneous connections of the signal emitting and receiving devices. This is further improved when the electrical connections to the transducers are integrated in the hose.

According to the invention the second objective is achieved by a method comprising supplying an acoustic signal at one side of the passage; receiving the acoustic signal at the other side of the passage, when the passage is open.

By the method according to the invention the opening can be determined very accurately as the reception signal is sampled and as the opening of the passage gives rise to a significant and unambiguous change in the received signal. The apparatus according to the invention may also be used in connection with the method and apparatus disclosed in U.S. Pat. No. 5,823,965 in order hereby to detect an obstruction in the bodily cavity. It is obvious that an erroneous diagnosis can be avoided by this combination.

The invention will be described more detailed in the following with reference to the drawing showing a preferred embodiment of the invention.

BRIEF DESCRIPTION OF THE DRAWINGS

FIG. 1 is a schematic view of an apparatus according to the invention;

FIG. 2 is a perspective view of a tube part of the apparatus of FIG. 1;

DESCRIPTION OF THE PREFERRED EMBODIMENT

Figure 4:
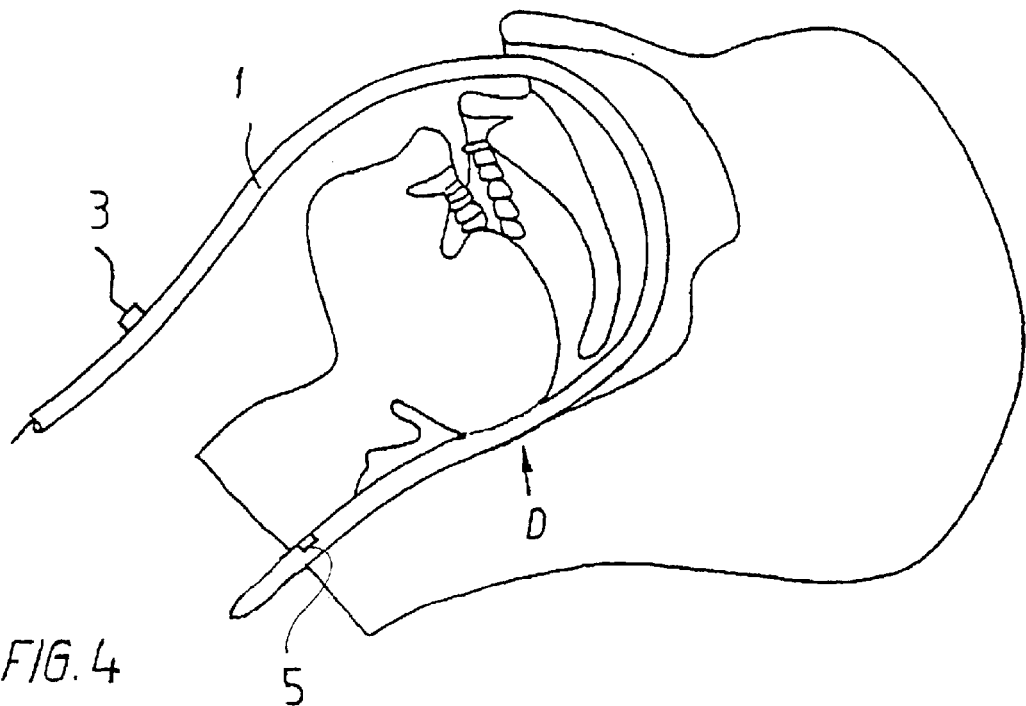
FIG. 4 is a further schematic view of the apparatus of FIG. 1 in a state of use where the obstruction shown in FIG. 3 has been eliminated.
Figure 3:
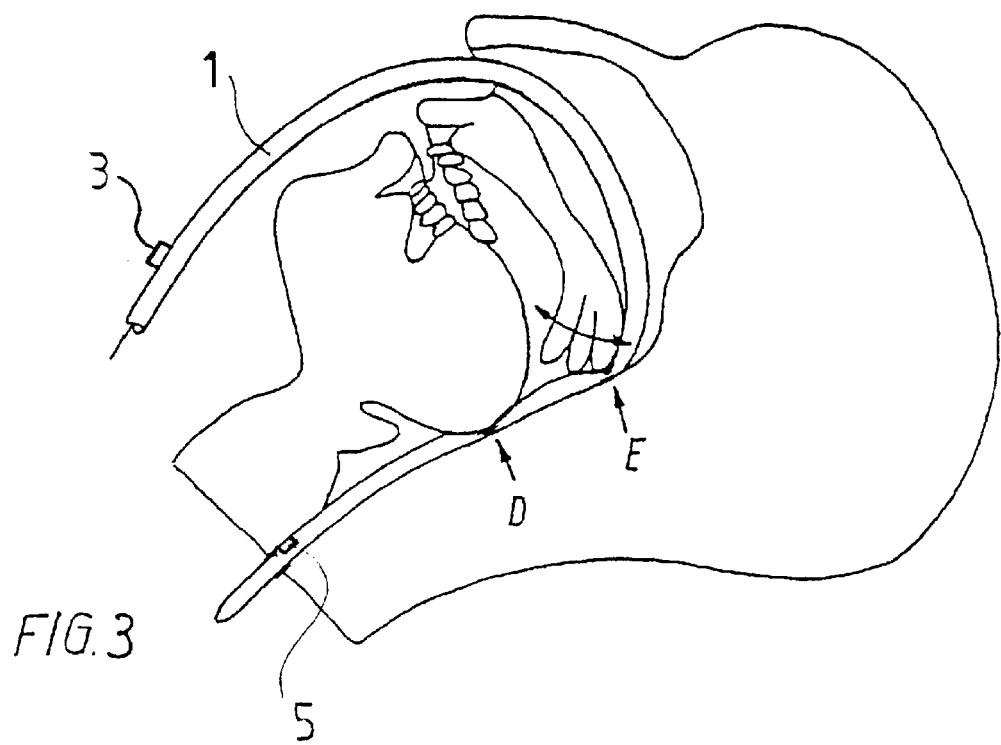
FIG. 3 is a schematic view of the apparatus of FIG. 1 in a state of use where an obstruction is indicated.

Referring to FIG. 1 the apparatus according to the invention comprises a signal generating unit 2 and a signal processing unit 4, a hose or catheter 1 and two transducers 3,5, i.e. a first emitting transducer 3, e.g. a speaker, and a second receiving transducer 5, e.g. a microphone. The transducers 3,5 are placed at respective ends, proximal end A and distal end B, of the hose 1 and are connected to the signal generating and processing units. The signal-processing unit is connected to a display 7 and a keyboard 6 for showing the measuring results and controlling the apparatus, respectively. Referring to FIG. 2 a measuring zone G of the hose 1 shown in FIG. 1 appears. It is clear that the wall material 9 allows movement in a radial direction F of the hose, hereby allowing the restriction to compress the hose and hence this will not have an erroneous impact on the measuring results. Referring to FIG. 3 the apparatus of FIG. 1 is shown in a mounted state where the hose or catheter 1 with the transducers 3,5 has been introduced into a bodily cavity, the respiratory passage, of a patient. The apparatus function in the following manner: a signal is generated in the signal-generating unit and is supplied to the first transducer, which emits an acoustic signal. When the passage is closed as shown in FIG. 3 at the rear part of the tongue at D and at the soft palate at E, the acoustic signal will not reach the second transducer or will only reach the second transducer as a weak signal. Once the passage is opened as shown in FIG. 4 the acoustic signal will immediately give rise to an increase in the level of the signal received by the second transducer. This is an unambiguous indication of the opening of the passage. The opening of the passage may be performed by supplying a pressure to the respiratory passage. This is not shown in FIG. 3 and FIG. 4. When supplying a pressure, which is gradually increased, e.g. in steps or continuously and when sampling the values for the pressure supplied and the opening state at the same time the relevant pressure for performing the opening may be determined very accurately. The signal generator 2 generates a characteristic signal, which is supplied to the transducer and to the signal processor. The signal received by the second transducer is compared with this in the signal-processing unit 4. Hereby erroneous measurements can be avoided, as only the receipt of the correct characteristic signal will result is a detection of an open passage.

What is claimed is:

1. A method for measuring opening of a passage in a bodily cavity having an obstruction, the method comprising:
    inserting a first transducer in the bodily cavity from a proximal side of the obstruction to a remote side beyond the obstruction,
    positioning a second transducer in said proximal side of the obstruction;
    supplying an acoustic signal to one of said first and second transducers; and
    receiving the acoustic signal at another of said first and second transducers, when the passage is open.

2. A method according to claim 1, comprising applying pressure to the bodily cavity such that the opening measurement is related to the pressure applied in a signal processing means.

3. A method according to claim 2, comprising increasing the pressure during the measurement and the opening measurement is carried out continuously.

4. A method according to claim 2, wherein atmospheric pressure is present on one side of the obstruction and providing an increased pressure an opposite side.

* * * * *